(12) United States Patent
Stauffer

(10) Patent No.: US 7,977,515 B2
(45) Date of Patent: Jul. 12, 2011

(54) FORMALDEHYDE SYNTHESIS

(76) Inventor: John E. Stauffer, Greenwich, CT (US)

( * ) Notice: Subject to any disclaimer, the term of this patent is extended or adjusted under 35 U.S.C. 154(b) by 0 days.

(21) Appl. No.: 12/828,383

(22) Filed: Jul. 1, 2010

(65) Prior Publication Data

US 2011/0105801 A1    May 5, 2011

Related U.S. Application Data

(63) Continuation-in-part of application No. 12/611,331, filed on Nov. 3, 2009, now Pat. No. 7,790,933.

(51) Int. Cl.
*C07C 45/30* (2006.01)

(52) U.S. Cl. .................. 568/472; 568/475; 568/490

(58) Field of Classification Search .................. 568/472, 568/475, 490
See application file for complete search history.

(56) References Cited

U.S. PATENT DOCUMENTS 7,790,933 B1 *   9/2010   Stauffer ................. 568/472

* cited by examiner

*Primary Examiner* — Sikarl Witherspoon
(74) *Attorney, Agent, or Firm* — Young Basile Hanlon & MacFarlane PC

(57) ABSTRACT

A process is disclosed for the synthesis of formaldehyde from methane starting with the oxychlorination of methane to produce methylene chloride. Hydrolysis of methylene chloride yields the product formaldehyde. Gaseous formaldehyde is condensed for shipment. Byproduct chloroform and carbon tetrachloride are recovered and hydrogenated to provide additional methylene chloride.

4 Claims, 2 Drawing Sheets

FORMALDEHYDE SYNTHESIS

CROSS-REFERENCE TO RELATED APPLICATION

This application is a continuation-in-part of the co-pending U.S. patent application Ser. No. 12/611,331 filed Nov. 3, 2009. The content of the U.S. patent Ser. No. 12/611,331 is incorporated herein by reference.

FIELD OF THE INVENTION

This invention relates to a process for manufacturing formaldehyde from methane. In the process, methane is first oxychlorinated with oxygen and hydrogen chloride to give chlorinated methane including methyl chloride, methylene chloride, chloroform and carbon tetrachloride. Methylene chloride is hydrolyzed with water to produce formaldehyde. Gaseous formaldehyde is converted to solid material in the form of trioxane or paraformaldehyde. The methyl chloride is recycled to the oxychlorination step while the chloroform and carbon tetrachloride are treated with hydrogen to produce more methylene chloride.

BACKGROUND OF THE INVENTION

Some formaldehyde is produced industrially by the oxidation of paraffin hydrocarbons, but the greatest amount is manufactured by the oxidation of methanol. When methanol is used as the raw material, two chemical reactions may be employed. In one process, a catalyst is used for the vapor-phase oxidation of methanol. In the other process, a combination of oxidation-dehydrogenation is used to convert methanol to formaldehyde.

Regardless of the process used to produce formaldehyde, certain disadvantages are inherent in existing technologies. The oxidation of hydrocarbons results in a complex mixture of products that are difficult to separate. Processes based on methanol are dependent on a raw material that fluctuates widely in availability and cost. Industrial grade formaldehyde is sold as aqueous solutions with concentrations ranging from 36 to 56 weight percent formaldehyde.

Therefore, it is an object of the present invention to provide for the synthesis of formaldehyde starting with methane, which is the main component of natural gas. The process should be both efficient and robust.

These and other objects, features and advantages of the present invention will become apparent from the following description taken with the accompanying figures.

SUMMARY OF THE INVENTION

A process is provided for the synthesis of formaldehyde beginning with methane. The process comprises separate reactions operated in concert.

In the first reaction, methane is oxychlorinated with oxygen and hydrogen chloride to produce chlorinated methane and water. The products include methyl chloride, methylene chloride, chloroform and carbon tetrachloride. This reaction is promoted by a catalyst.

The second reaction involves the reduction of chloroform and carbon tetrachloride with hydrogen to yield methylene chloride and hydrogen chloride. Various catalysts may be used for this reaction.

Finally, the third reaction comprises the hydrolysis of methylene chloride with water to form formaldehyde and hydrogen chloride. A catalyst is employed in this reaction. Gaseous formaldehyde so formed is concerted to solid material by an acid catalyzed reaction.

As noted, the first reaction produces methyl chloride, which can be recycled to the oxychlorination reaction to produce additional methylene chloride. A stand-alone process is achieved by recycling hydrogen chloride produced in the second and third reactions to the first reaction. In this manner there is no net consumption of chlorine values.

BRIEF SUMMARY OF THE DRAWINGS

The description herein makes reference to the accompanying drawings wherein like reference numerals refer to like parts throughout the several views and wherein.

DETAILED DESCRIPTION OF THE ILLUSTRATIVE EMBODIMENT

Three separate reactions, operated in tandem, are employed to convert methane to formaldehyde in high yields. By understanding the chemistry involved, a better appreciation of the merits of the process can be obtained.

The first reaction step, known as oxychlorination, achieves the chlorination of methane and recycled methyl chloride using as the source of chlorine. A catalyst is needed and can comprise a copper salt. Because of the poor reactivity of methane, a sufficiently high reaction temperature is required, usually in excess of 375° C.

The distribution of products from the first reaction step can be controlled only within broad ranges. Thus, although the object is to produce methylene chloride, inevitably some methyl chloride, chloroform and lesser quantities of carbon tetrachloride will be produced. In addition, some methane usually escapes unreacted.

Depending on market conditions, there may be a demand for the byproducts methyl chloride, chloroform and carbon tetrachloride. However, this situation cannot be relied on, particularly for a large installation. Therefore, the recovery of chloroform and carbon tetrachloride is critical to the success of the process.

Chloroform and carbon tetrachloride are recovered by reacting these products with hydrogen in a second reaction step to give methylene chloride and hydrogen chloride. The equilibrium conditions for these reactions are extremely favorable. Specifically, in the reduction of chloroform with hydrogen to form methylene chloride and hydrogen chloride log $K_p$ equals 10.98 at 200° C. and has a value of 8.25 at 400° C.

Figure 1:
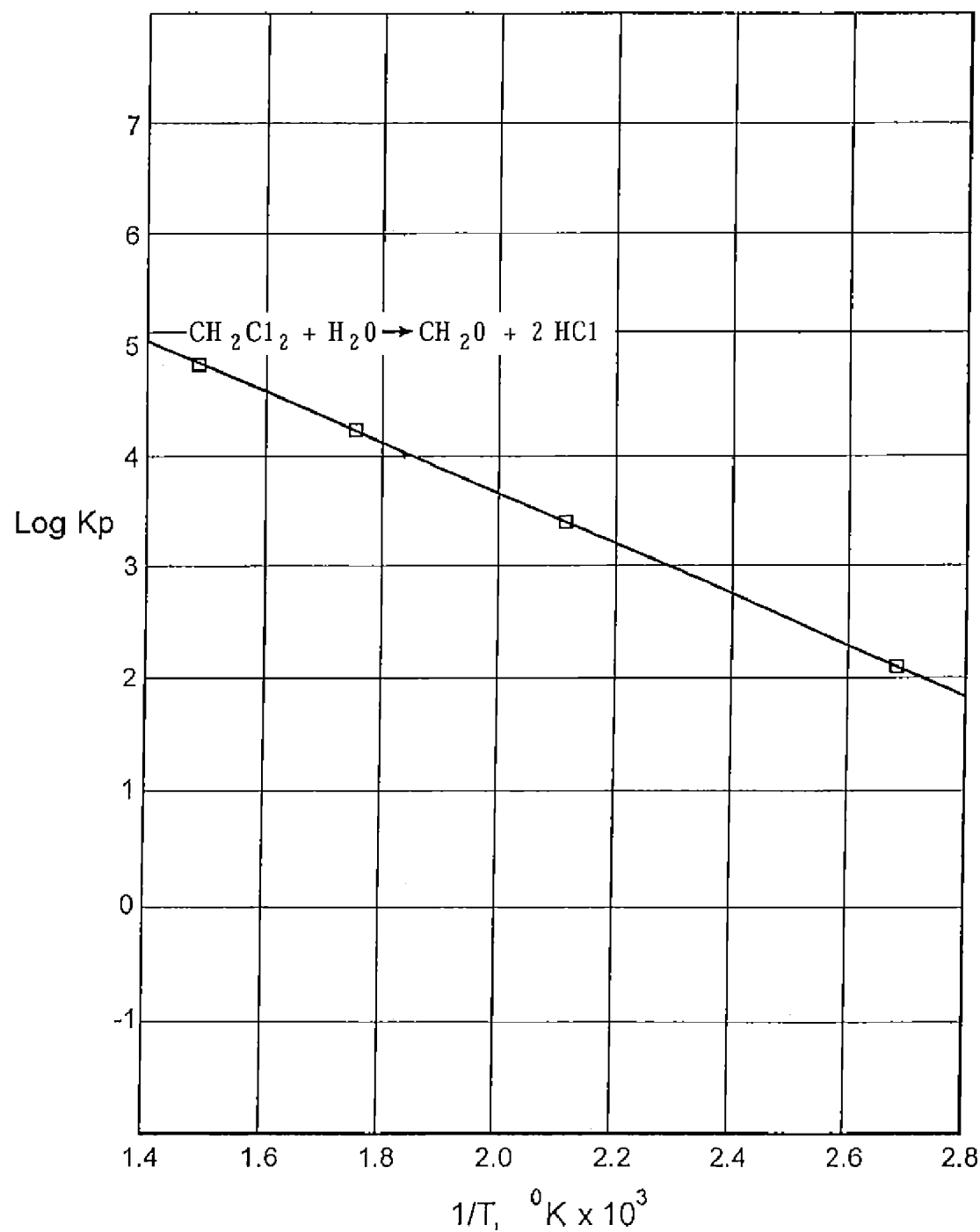
FIG. 1 is a graph showing the conversions at equilibrium of methylene chloride to formaldehyde by undergoing hydrolysis with water.

Although hydrogenation can be conducted by a free radical reaction, a catalyst may be used to advantage. Prime candidates for catalysts are the transition metals. These elements, in forming compounds, exhibit multiple oxidation states. Among the transition elements of interest are cobalt, molybdenum, nickel, iron, and platinum. In the third reaction step, methylene chloride is hydrolyzed with water to produce formaldehyde and hydrogen chloride. As indicated by the data in FIG. 1, the yield of product is quite favorable. Thus, at 200° C. log $K_p$ for the reaction equals 3.40 while at 400° C., log $K_p$ is 4.83.

Because methylene chloride is relatively stable, a catalyst is required for the hydrolysis reaction. Several catalysts are usable, including activated carbon and tin phosphate. This list, however, is not meant to be limiting. Conceivably, any catalyst used for the hydrolysis of methyl chloride might be considered. These include alumina gel and zinc chloride.

The product of the hydrolysis reaction is gaseous formaldehyde. Because this gas is difficult to transport long distances it is first converted to a solid substance. By means of an acid catalyzed reaction, gaseous formaldehyde is condensed to either the trimer trioxane or the polymer paraformaldehyde. Formaldehyde is easily reconstituted from these solid substances on demand.

Figure 2:
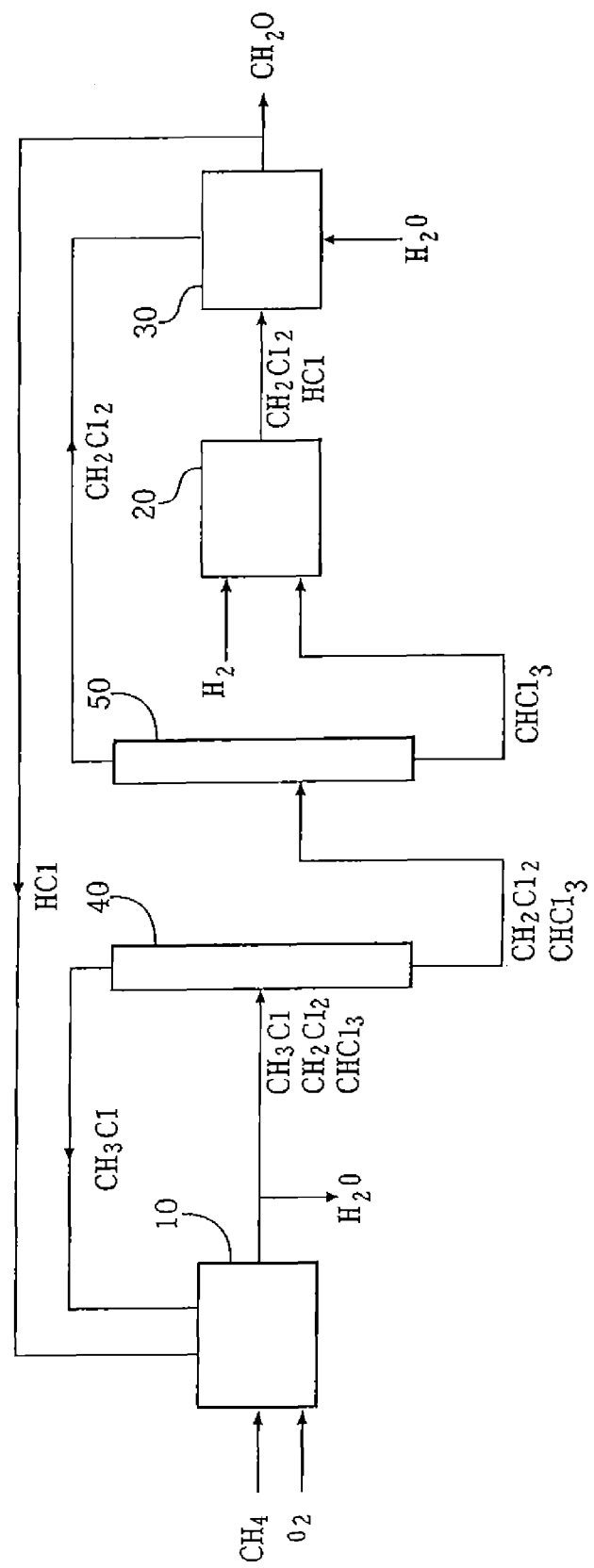
FIG. 2 is a schematic flow sheet of the process showing the principal reactors and the auxiliary equipment.

The process of the present invention can best be visualized by referring to the simplified flow sheet in FIG. 2. In this illustration, reactor 10 is used for oxychlorination, reactor 20 for hydrogenation, and reactor 30 for hydrolysis. Distillation columns 40 and 50 provide the separation and purification of the components in the streams shown. For the sake of clarity, some details are omitted. For example, in the methyl chloride recycle stream, some methane may be present. Also, the chloroform stream from distillation column 50 will probably contain carbon tetrachloride. Likewise missing from the flow sheet is the condensation of formaldehyde to solid material.

The present invention represents a comprehensive solution to the manufacture of formaldehyde from methane. The only required raw materials are methane, hydrogen and oxygen or air. There are no byproducts or waste streams that must be handled. In this balanced operation, maximum efficiency is attained. Finally, the chemistry is straightforward and easy to scale up to a commercial unit.

What is claimed is:

1. A process for the synthesis of formaldehyde from methane comprising the following steps operated in concert:
   a. the reaction of methane and methyl chloride with oxygen and hydrogen chloride in the presence of a catalyst to give methylene chloride,
   b. the reaction of methylene chloride with water in the presence of a catalyst to form gaseous formaldehyde and hydrogen chloride; and
   c. the condensation of gaseous formaldehyde to a solid material.

2. A process according to claim 1 in which the solid material is trioxane.

3. A process according to claim 1 in which the solid material is paraformaldehyde.

4. A process for the synthesis of formaldehyde from methane comprising the following steps operated in concert:
   a. first, the reaction of methane with oxygen and hydrogen chloride in the presence of a catalyst to give methylene chloride and water,
   b. second, the reaction of methylene chloride with water in the presence of a catalyst to form formaldehyde and hydrogen chloride, and
   c. third, the use of the hydrogen chloride produced in the second reaction as a starting material for the first reaction.

* * * * *